United States Patent [19]

Zahniser et al.

[11] Patent Number: 5,168,066
[45] Date of Patent: Dec. 1, 1992

[54] THIONIN STAINING AND IMAGING TECHNIQUE

[75] Inventors: David J. Zahniser, Wellesley; Daniel C. Lapen, Lancaster, both of Mass.; Petrus S. Oud, Bennebrooek, Netherlands

[73] Assignee: Cytyc Corporation, Marlborough, Mass.

[21] Appl. No.: 797,312

[22] Filed: Nov. 25, 1991

Related U.S. Application Data

[63] Continuation-in-part of Ser. No. 490,087, Mar. 7, 1990, abandoned.

[51] Int. Cl.$^5$ .................... G01N 1/30; G01N 21/00
[52] U.S. Cl. .................... 436/63; 436/166; 436/172; 436/174; 424/3; 382/6; 356/36; 356/51
[58] Field of Search ............ 436/17, 63, 64, 166, 436/72, 174, 800, 813; 424/3, 7.1; 382/1, 6; 356/36, 51, 39

[56] References Cited

U.S. PATENT DOCUMENTS

| | | | |
|---|---|---|---|
| 4,395,493 | 7/1983 | Zahniser et al. | 435/289 |
| 4,595,582 | 6/1986 | Balogh et al. | 424/3 |
| 4,998,284 | 3/1991 | Bacus et al. | 382/6 |

FOREIGN PATENT DOCUMENTS

1178183 11/1984 Canada .

OTHER PUBLICATIONS

Oud, P. S. "The use of Light Green and Orange II as quantitative protein stains, and their combination with the Feulgen method for the simultaneous determination of protein and DNA" Histochemistry, vol. 80 (1984) pp. 49–57.

MacAuley et al., *Analytical and Quantitative Cytology and Histology*, vol. II, Feb. 1989, pp. 53–58.

Oud et al., *Cytometry* 7:8–17 (1986).

Stormer et al., *Acta Histochem.* 79:127–134 (1986).

Garbay et al., *Analytical and Quantitative Cytology and Histology*, vol. 8, Mar. 1986, pp. 25–34.

Oud et al., *Analytical and Quantitative Cytology*, vol. 6, No. 2, Jun. 1984, pp. 131–138.

Oud et al., *Analytical and Quantitative Cytology*, vol. 3, No. 4, Dec. 1981, pp. 289–294.

Holmquist et al., *The Journal of Histochemistry and Cytochemistry*, vol. 24, No. 12, 1976, pp. 1218–1224.

Oud, Doctoral Thesis, University of Nijmegen, Netherlands, 1986.

Zahniser, Doctoral Thesis, University of Nijmegen, Netherlands, 1979.

Puchtler, H. et al., "Infrared Fluorescence Microscopy of Stained Tissues: Principles and Technique", Histochemistry, vol. 68 (1980) pp. 211–230.

*Primary Examiner*—James C. Housel
*Assistant Examiner*—Jeffrey R. Snay
*Attorney, Agent, or Firm*—Lahive & Cockfield

[57] ABSTRACT

Cellular analysis in accordance with the invention involves staining cellular material with a thionin stain to distinguish the nuclear portion from the cytoplasm, counterstaining, illuminating the thionin-stained cellular material with energy in the infrared spectrum, and imaging the stained cellular material. The analysis can be automated or manual.

15 Claims, 6 Drawing Sheets

THIONIN STAINING AND IMAGING TECHNIQUE

This application is a continuation-in-part of Ser. No. 490,087, filed Mar. 7, 1990, now abandoned.

FIELD OF THE INVENTION

This invention relates to the analysis of cellular material. Specifically, this invention relates to a method of staining cells for cytological or histological analysis to contrast the nuclear portion of the cell from the cytoplasmic portion. The analysis can be automated or manual.

BACKGROUND OF THE INVENTION

A traditional multicolored stain is desirable for staining cell smears for certain cytological analyses. It is advantageous because the nucleus and the cytoplasm of the stained specimen are colored differently. In one preferred staining practice, the cytoplasm is transparent, whereas the nucleus is transparent to opaque. This staining pattern allows the cytologist to distinguish cells which are morphologically abnormal. In addition, cytologists find the variety of colors of the traditional stains, particularly the Papanicolaou stain, helpful to reduce eye strain and to aid diagnosis.

However, the traditional stains, including the Papanicolaou stain, are difficult for an automated system to analyze. The variety of colors in the cytoplasm from traditional stains, which are straightforward for the human eye to distinguish, are not readily analyzed with automated systems because they contrast to varying degrees with the traditional blue hematoxylin stain of the nucleus. The varying contrast makes automated analysis unreliable.

A number of researchers have developed algorithms in an attempt to attain automated analysis of cells stained with the Papanicolaou stain. Most techniques involve the use of various instrumental artifacts, such as different colors of light, filters, and color television cameras. Many require a high level of sophistication that is costly in terms of hardware and software. Further, these approaches have not proven accurate and reliable enough to be widely used in clinical cytological and histological diagnoses.

It is an object of the present invention to provide a method of cellular analysis in which the cells are multicolored and the nuclear portion is clearly distinguishable from the cytoplasmic portion both with automated equipment and with manual vision analysis.

It is a further object to provide a method of cellular analysis in which the characteristics of the stained cells can be accurately determined with both manual and automated analysis procedures.

Other objects of the invention will in part be obvious and will in part appear hereinafter.

SUMMARY OF THE INVENTION

The method of cellular analysis in accordance with the invention can be used as part of an automated analysis system and for manual analysis. It entails staining cellular material with a thionin stain that clearly contrasts the nuclear portion from the cytoplasmic portion under infrared illumination. In a further step, the cellular material is counterstained with a stain that absorbs infrared light at a level distinguishable from that of the thionin stain. Another step involves illuminating the stained cellular material with energy in the infrared spectrum, and a further step involves imaging the stained cellular material with the output energy from the interaction of the infrared energy with the stained cellular material.

The improvement of this method over the art includes illuminating the cellular material, previously stained with the thionin stain, with energy in the infrared spectrum. It has now been found that a mildly acidic, organic thionin stain compound can be strongly absorbing in the infrared spectral region when bound to nuclear material. This allows physiological parameters of the individual cell components, i.e., size, configuration and texture, to be distinguished and analyzed under infrared illumination. The imaging step preferably includes detecting the output energy with a light-sensing, opto-electric transducing device which may include photomultipliers, solid-state photo-detectors, detector arrays, and television cameras. The imaging step preferably includes digitizing the transduced image, for computerized analysis and pathological diagnosis of the stained cellular material.

The thionin stain used in the method of the invention consists of a thionin salt, an organic solvent, and a pH buffer. The thionin salt is preferably thionin acetate, and thionin bromide and thionin perchlorate are also effective. The organic solvent is a low molecular weight alcohol or DMSO, where the alcohol is preferably a reagent grade alcohol, and is preferably methanol. One preferred pH buffer is prepared with glacial acetic acid, distilled water, and 5N NaOH to about pH 4.9. However, other buffers having a pH in the range of from about pH 3 to about pH 9 such as Tris ®, AMP, glycine, and KOH are effective.

The thionin stain is used in combination with a counterstain that manifests the cytoplasmic portion under visible light. In one practice of the invention, the cellular material is stained with the thionin compound, rinsed in a low molecular weight alcohol, and then counterstained with a traditional Papanicolaou stain. In another practice of the invention, the counterstain is an eosin-type stain.

The Papanicolaou stain, when applied to cells stained with the thionin stain, produces the multicolored cells obtained from staining with the traditional Papanicolaou alone. This particular combination of the thionin stain and the Papanicolaou stain provides a system useful both for human visual analysis and for automated analysis. Further, the automated analysis and characterization of the cell can be carried out without the need for costly hardware and/or software. The cytoplasm can be analyzed under visible light and the nucleus can be analyzed under infrared illumination.

A similar advantage is obtained by staining the cell first with a thionin stain and then with a counterstain which is an eosin-type stain. This thionin-eosin stain replaces the traditional H-E (hematoxalin-eosin) histological stain with one that gives the same visual effect as the H-E stain, and has the added advantage of distinguishing the nucleus from the cytoplasm under infrared light. Incorporating the method of the present invention into conventional counterstaining techniques, such as the Papanicolaou stain and the eosin-type stain, produces visible staining patterns familiar to cytologists. The combination has the added advantage of being capable of use with an automated cell analysis system to produce reliable and accurate results which can be used in pathological procedures including, for example, in the detection of cervical cancer.

BRIEF DESCRIPTION OF THE DRAWINGS

For a fuller understanding of the nature and objects of the invention, reference should be made to the following detailed description taken in connection with the accompanying drawings, in which.

DETAILED DESCRIPTION

A method of staining cellular material according to the invention provides improved contrast of the nucleus from the cytoplasm. The method produces the traditional multicolored cells suitable for manual analysis, and is highly effective in automated analysis systems. The method entails the steps of staining the cellular material with a thionin stain, counterstaining, illuminating the thionin-stained material with energy in the infrared spectrum, and imaging the stained cellular material.

Figure 1:
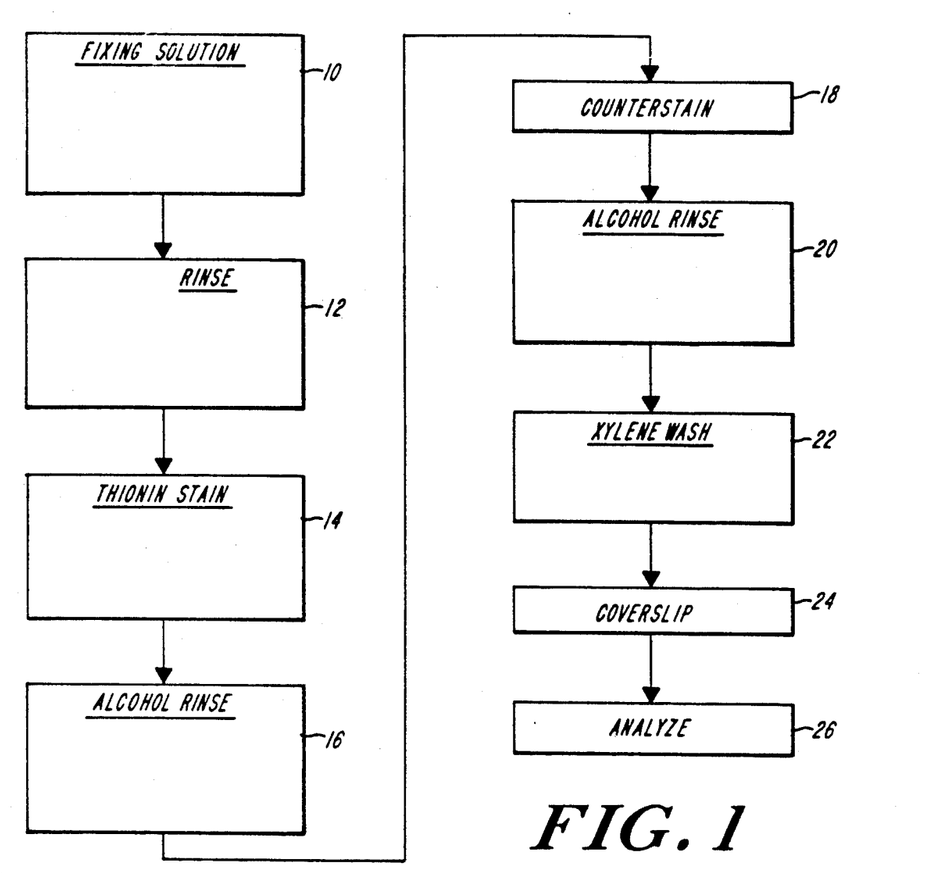
FIG. 1 is a flow chart depicting the general staining technique of the present invention.

In one practice of the invention, the cells are stained by the general method shown in FIG. 1. The cells are fixed on the slide, step 10, rinsed in alcohol or water baths, step 12, and stained with a thionin stain, step 14. The stained cells are rinsed in alcohol baths, step 16, and counterstained, step 18. After counterstaining, the stained cells are rinsed in alcohol, step 20, and rinsed in xylene or other commercially available xylene substitutes, step 22, before the coverslip is applied, step 24.

Figure 3:
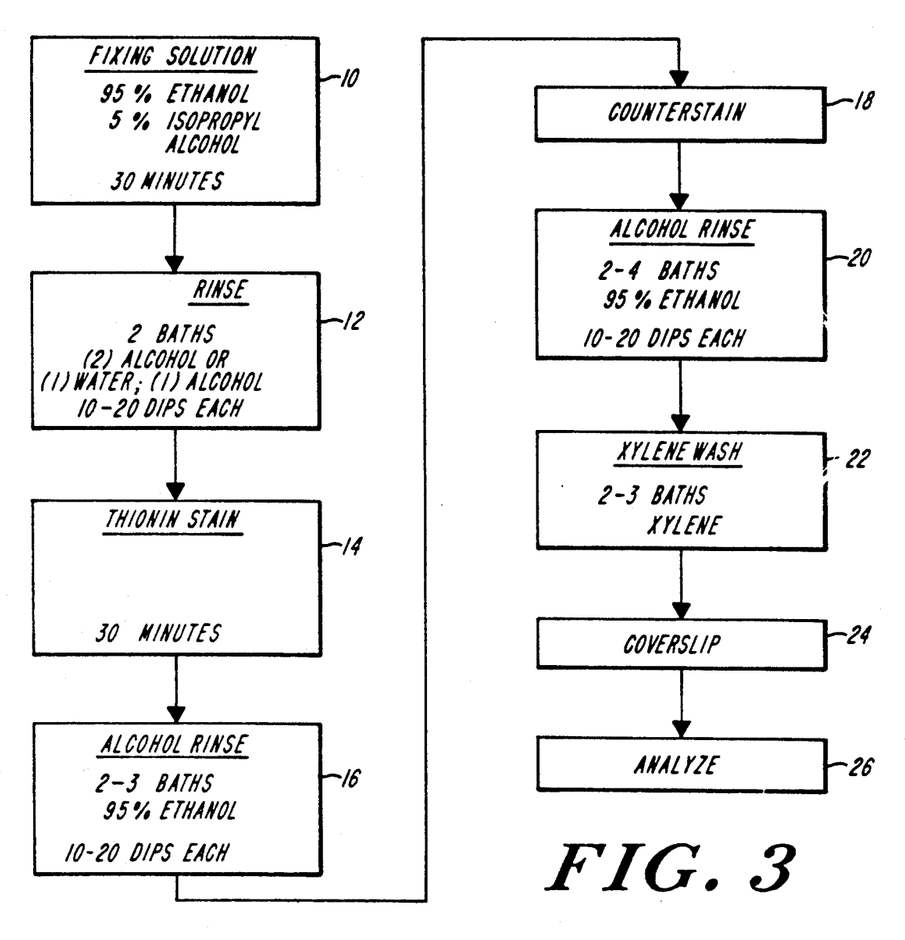
FIG. 3 is a flow chart depicting one staining technique of the present invention.

As shown in FIG. 3, the cells are first fixed on the slide, using alcohol or other methods known in the art, step 10. Then, in preparation for staining, the slide is dipped ten to twenty times in each of two baths where is one is a high percentage, low molecular weight alcohol, which is preferably ethanol, and the other is an alcohol bath or a water bath, step 12. The cells are stained in a thionin stain solution, step 14, for a time sufficient to incorporate the thionin dye in the nuclei, which may range from three minutes to five hours, but typically is about thirty minutes. Those skilled in the art will recognize that the staining time can be determined by taking several factors into account, including the desired intensity of the stain appropriate for the cell type and the viewing system used. Automated systems generally require darker staining than human visual evaluation, and certain types of cells stain faster than others. Also, the amount of thionin in the stain can affect the staining time. Lower concentrations of thionin will generally require longer staining times.

After rinsing by dipping ten to twenty times in each of two to three high percentage, low molecular weight alcohol baths, preferably two baths, followed by a third bath lasting approximately five minutes in a high percentage, low molecular weight alcohol, step 16, the cells are counterstained, step 18. That is, the cells are stained with one or more dyes that are primarily taken up by the cytoplasm. When combined with nuclear material, and at a pH typically in the range of pH 4-9, thionin dye absorbs infrared light. A thionin stain preferred for most cells is slightly acidic, typically having a pH of about 6.45. The counterstain is selected to absorb at a different wavelength from the thionin-stained nuclear material. After staining and counterstaining, the slide is rinsed by dipping in two to four more high percentage, low molecular weight alcohol baths, step 20, and two or more xylene rinses or other commercially available xylene substitutes, step 22, before the coverslip is applied, step 24, and the cells are ready to be analyzed, step 26.

When viewed under visible light, the nuclei of the cells are transparent to opaque and stained a deep blue. The cytoplasm is transparent and is multicolored, with the specific color pattern depending on the counterstain used. When cells are stained in this manner, the color pattern is familiar to cytologists, so analysis can readily be carried out by manual, i.e., human, vision. The method has the added advantage in that, when viewed under infrared light, each nucleus is opaque, and the cytoplasm is nearly invisible. With the cytoplasm nearly invisible, overlapping cells will not be confused with nuclei, and an accurate cell count can be easily achieved, manually or by computer.

Solid state television cameras and other opto-electric transducers that are sensitive to infrared energy are employed in the next step, 26, to image the output energy from the stained cells. The image can be digitized for a completely automated analysis and can also be viewed on a display monitor. The nuclear components of the cell are distinguishable and the cells can be measured and classified, e.g., as malignant or as benign.

Figure 2:
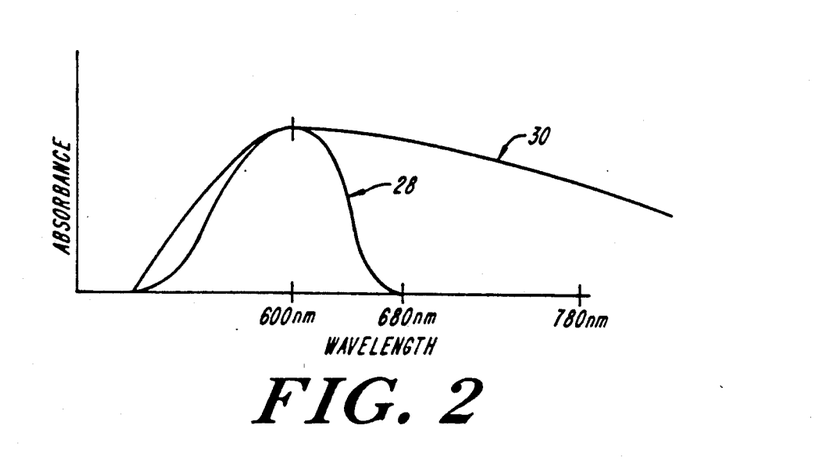
FIG. 2 is a graph depicting the absorbance and wavelength of the thionin stain alone and of the thionin stain bound to the nucleus.

The thionin stain and method of staining is believed to be primarily responsible for this phenomenon. Thionin alone is not known to absorb infrared light, nor to do so when mixed as a dye or when bound to the nucleus in a Feulgen-type reaction, a highly acidic nuclear stain. However, it has been found that a thionin stain in a buffered solution with a selective acidic range binds only to the nucleus, and becomes strongly absorbing in the near-infrared range. As shown in FIG. 2 with waveform 28, a thionin stain by itself has maximal absorption at 600 nm (visible red light), and is almost transparent at around 680 nm. When bound to the nucleus, however, the spectrum of absorbance extends to longer wavelengths, as indicated with waveform 30. Peak absorbance remains at about 600 nm, but the nuclear-bound thionin continues to absorb into the near-infrared range, and at 780 nm, the stained nucleus is absorbing 60-70% of its peak.

The thionin stain for practice of the invention can be essentially a thionin salt, an organic solvent such as DMSO or a low molecular weight alcohol, and a pH buffer having a pH in the range of about 3-9. The thionin salt may be the bromide or the perchlorate, and preferably is the acetate. In one embodiment, the thionin stain is mace of approximately eighty parts of solution A and approximately twenty parts of solution B (1×Buffer) or $B_1$ (4×Buffer), as prepared according to the following Table I. Solution A as a thionin concentration ranging from about 0.5 g/l to about 30 g/l, and alcohol, preferably methanol, in the range of about 80% to about 20%. One suitable formula is prepared as set forth in Table I by stirring overnight and then filtering over Whatmann No. 5 filed paper or equivalent.

TABLE I

| Solution A | |
|---|---|
| Thionin acetate (Aldrich) | 0.50 gm |
| Methanol (analytical grade) | 100 ml |
| Solution B | |
| Glacial acetic acid | 8 ml |
| 5 N NaOH | 18 ml |
| Distilled water (pH = 4.9) | 74 ml |
| Solution B1 | |
| Glacial acetic acid | 37 ml |
| 5 N NaOH (pH = 5.24) | 63 ml |

The pH of the thionin solution ranges from about 4-9 and is preferably approximately 6-7. A thionin stain made of eighty parts solution A and twenty parts solution B is slightly acidic at pH=6.4+/−0.1. A stain made with eighty parts solution A and twenty parts solution $B_1$, has a slightly lower pH at 6.43. An alternative stain formulation, made with eighty parts solution A, five parts solution B, five parts DMSO, and ten parts water, has a pH of 6.8.

The preferred formulation for the thionin stain, Solution C, is preferred by stirring 13.3 ml acetic acid with twenty-four gm Tris ® base and 650 ml water until the reagents are dissolved. Methanol is added to a final volume of 1000 ml, after which ten gm thionin dye is added and stirring continues for about one hour. The solution is then filtered through a Gelman filter. The final pH is about 6.5.

The practice of the invention may be more clearly seen from the following non-limiting examples.

EXAMPLE I

Papanicolaou-type Stain

One preferred practice of method of the invention combines the thionin stain with the familiar Papanicolaou-type counterstain to attain effective automated analysis. The resultant multicolored stained cells, under visible light, are familiar to cytologists. The traditional Papanicolaou stain is difficult for automated systems to analyze because the variety of colors it produces with the cytoplasm, e.g., blue, green, red, and orange, contrast to varying degrees with the blue stain traditionally used for staining the nucleus. When this blue stain is omitted, in accordance with the invention, and the thionin stain with its unique infrared absorbance is substituted, reliable and accurate automated segmentation, i.e., locating and categorizing the nucleus, is relatively simple. The cytoplasm is analyzed under visible light and segmentation is performed under infrared light, to which solid state television cameras, solid state photodetectors, and other opto-electric transducing devices are especially sensitive. The resultant image can be digitized, and a cytological analysis can be carried out by computer. Because the stain appears under visible light like the familiar Papanicolaou stain, cytologists can monitor the computerized analysis.

Figure 4:
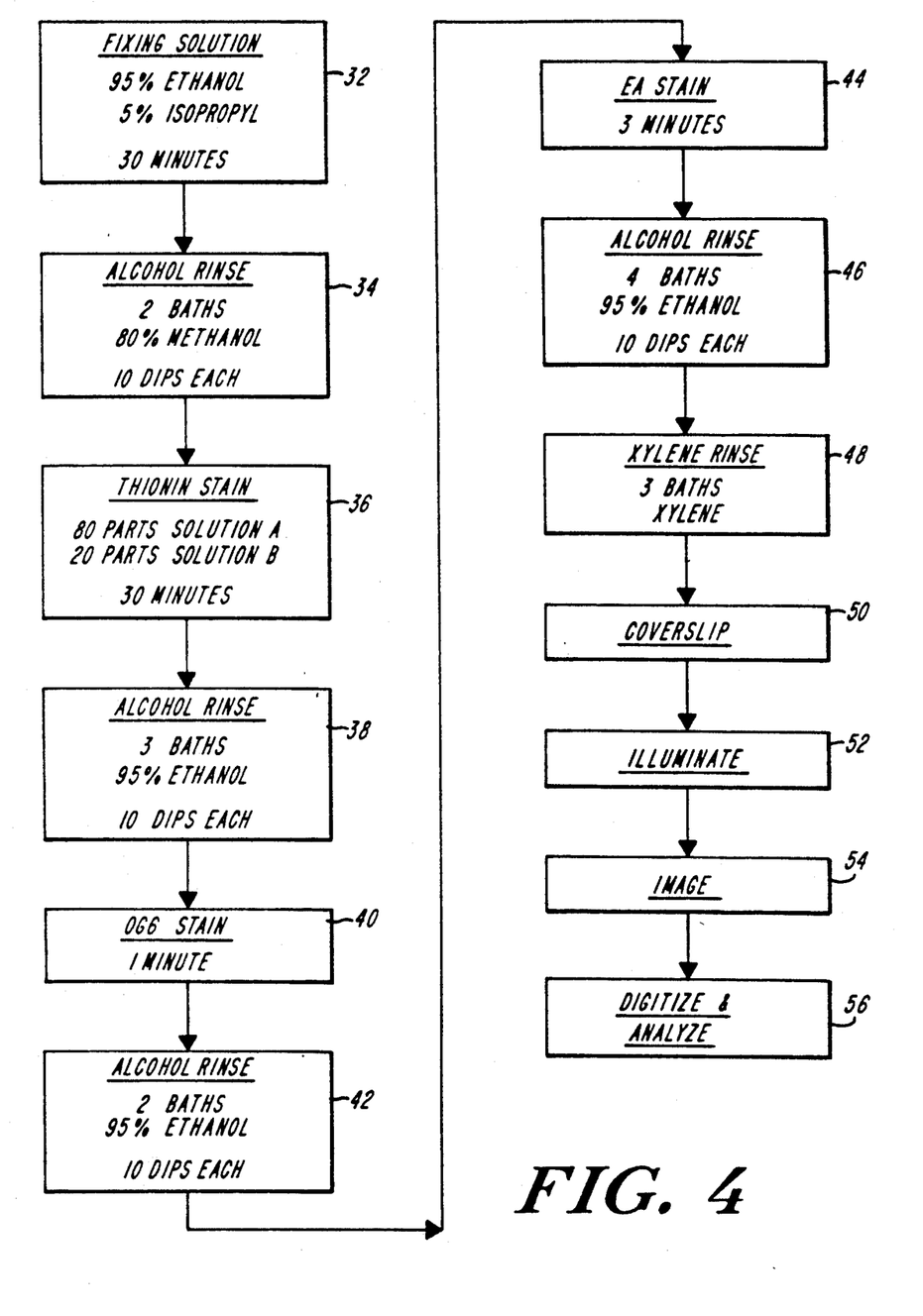
FIG. 4 is a flow chart depicting the staining technique of the present invention where a Papanicolaou-type counterstain is used.

As shown in FIG. 4, the cells are fixed on the slide, step 32, and then the cells are rinsed, step 34, in two separate alcohol baths, prior to staining with a thionin stain, step 36. The stained cells are rinsed in three separate alcohol baths, step 38, stained in the OG6 counterstain, step 40, and rinsed in two alcohol baths, step 42, before staining with an EA solution, step 44. After staining the cells are rinsed in two to four separate alcohol baths, step 46, followed by two to three xylene rinses, step 48, and a coverslip or other method of permanent mount, step 50, completes the staining process. After staining, the stained cells are illuminated with infrared light to segment the nucleus, step 52. Imaging step 54 is followed by digitizing step 56 for automated analysis.

In this preferred embodiment, the cells are fixed on the slide using an alcoholic fixing solution or other methods known in the art, step 32. The cells are rinsed by dipping the slide ten to twenty times in each of two separate 80% methanol baths, step 34, prior to staining with the thionin stain, prepared according to any of the above formulations, but preferably prepared according to the formulation for Solution C. After staining for approximately thirty minutes in the thionin stain, step 36, the slides are rinsed by dipping ten to twenty times, in each of two to three separate 95% ethanol baths, step 38, before staining with an OG6 solution, step 40. The OG6 stain is known in the art and is commonly used in Papanicolaou stains. A commercial OG6 stain (Baxter "SP") works well, or it may be preferably prepared by mixing together the ingredients listed in Table II.

TABLE II

| Ingredients | Amounts |
|---|---|
| Orange G dye | 0.5 g |
| Ethanol | 100 ml |
| Acetic acid | 1-5 ml |

After staining in the OG6 solution for one minute, the slide is rinsed by dipping ten to twenty times in each of two 95% ethanol baths, step 42, before being stained in an EA solution, step 42, before being stained in an EA solution, step 44. This solution, also well known in the art for use in the Papanicolaou staining technique, may be purchased (EA50, Baxter) or prepared by mixing the ingredients listed in Table III.

TABLE III

| Ingredients | Amounts |
|---|---|
| Eosin Y dye | 0.18 g |
| Light Green dye | 0.07 g |
| Phosphotungsic acid | 0.30 g |
| Ethanol | 50 ml |
| Distilled water | 50 ml |

After staining in the EA solution for three minutes, the slide is rinsed by dipping ten to twenty times in each of two to four separate 95% ethanol baths, step 46. This is followed by two to three xylene rinses, step 48, and then followed by coverslipping or other means of permanent mounting known in the art, step 50.

After staining, the cells are illuminated with infrared light to segment the nucleus, step 52. The output energy is imaged for cytological analysis, step 54. The image can be digitized and the analysis is carried out by computer, step 56.

EXAMPLE II

Thionin-eosin Stain

A second preferred embodiment employs an eosin-type counterstain. When used together, the thionin-eosin stain replaces the standard histological stain, the H-E (hematoxylin-eosin) stain, with one that is easy to analyze with an automated system.

The fixing, rinsing and thionin staining steps are the same as described above and are shown in FIG. 5, steps 58-62. After the thionin staining step, the cells are rinsed by dipping ten to twenty times in each of two to three 95% ethanol baths, step 64. The cells are stained in an eosin solution, step 66, prepared by mixing the ingredients found in Table IV. The rinsing, illumination and imaging steps are carried out as described above in Example 1 and shown in FIG. 4, steps 68-78.

TABLE IV

| Ingredients | Amounts |
| --- | --- |
| Eosin Y dye | 1.0 g |
| Methanol | 80.0 ml |
| Glacial acetic acid | 1.6 ml |
| Distilled water | 18.4 ml |

EXAMPLE III

Paparicolaou-type Stain

Figure 6:
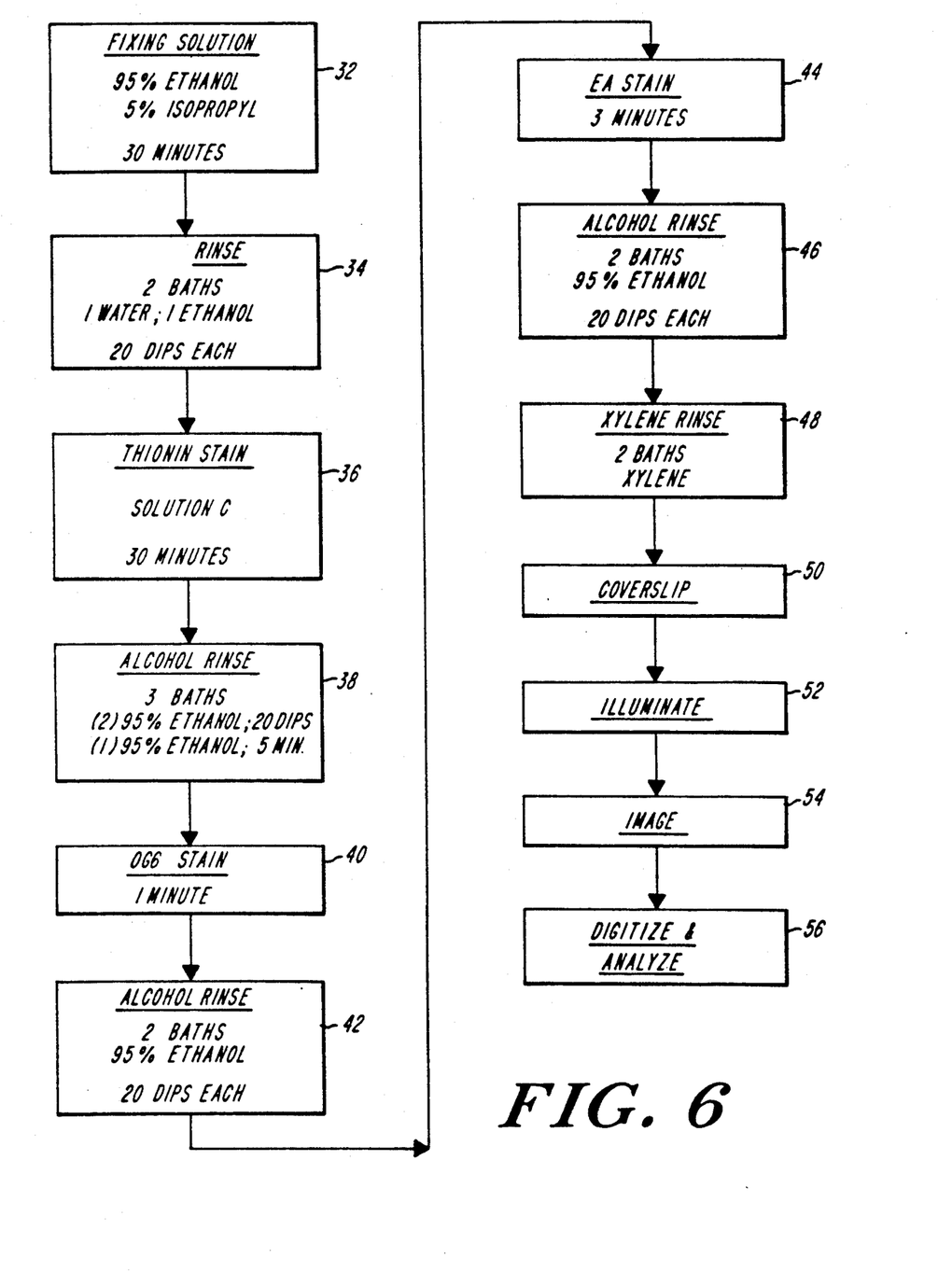
FIG. 6 is a flow chart depicting an alternative staining technique of the present invention using a Papanicolaou-type counterstain.

FIG. 6 shows a practice of the invention in the manner of FIG. 3 and deemed preferable and alternative to the embodiment of FIG. 4 and Example I.

EXAMPLE IV

Thionin-eosin Stain

Figure 5:
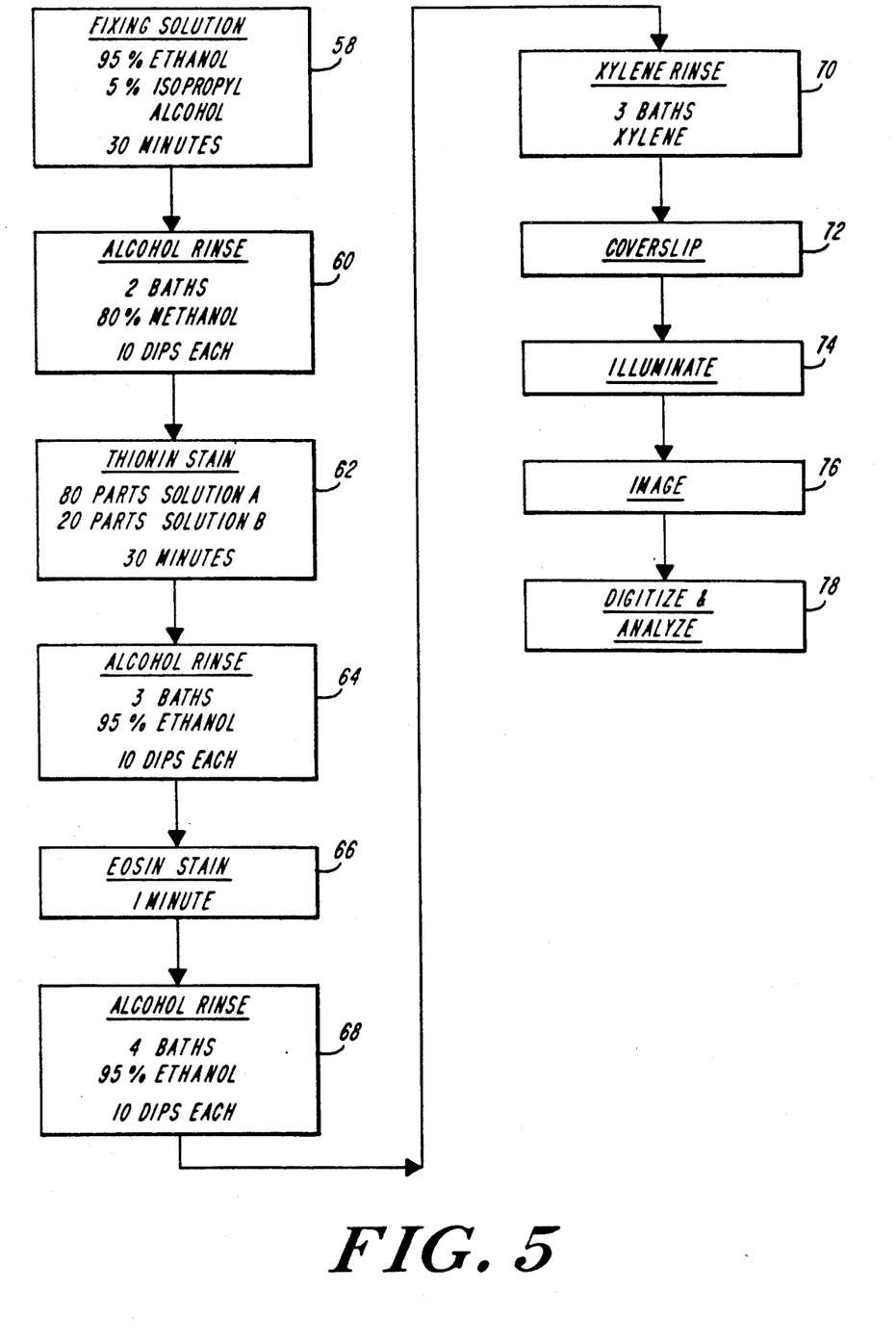
FIG. 5 is a flow chart depicting the staining technique of the present invention where an eosin-type counterstain is used.
Figure 7:
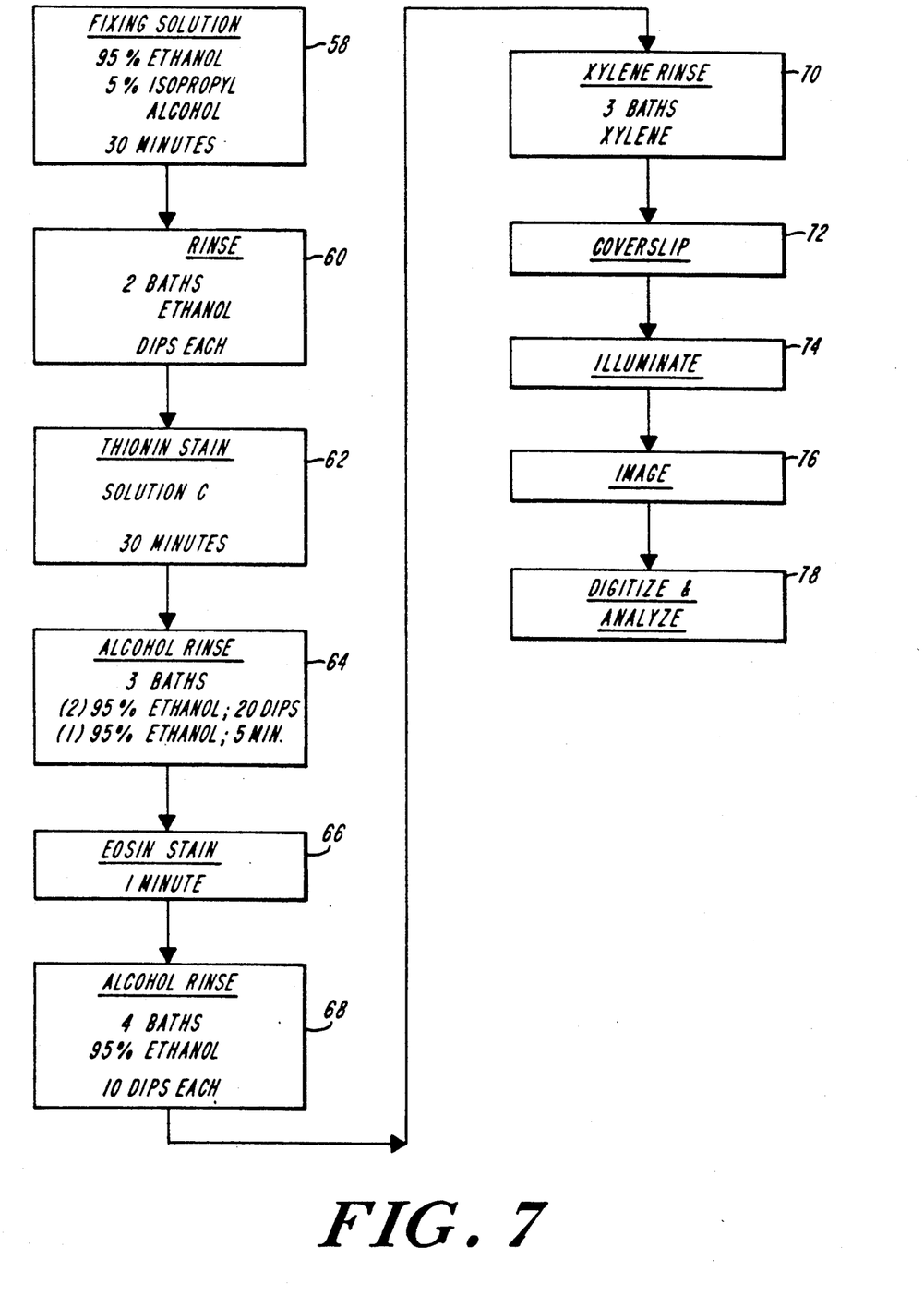
FIG. 7 is a flow chart depicting an alternative staining technique of the present invention using an eosin-type counterstain.

FIG. 7 shows a Practice of the invention in the manner of FIG. 3 and deemed preferable and alternative to the embodiment of FIG. 5 and Example II.

It will thus be seen that the objects set forth above, among those made apparent from the preceding description, are efficiently attained and, since certain changes may be made in carrying out the above method without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Having described the invention, what is claimed as new and secured by Letters Patent is:

1. A method of staining cellular material for contrasting nuclear material from cytoplasmic material, for producing stained cellular material suitable for automated machine analysis, and for imaging the stained cellular material, said method comprising the successive steps of
    staining the cellular material with an organic thionin stain having a predetermined pH in the range selected from about pH 4 to about pH 9 such that said thionin stain binds distinguishably more to said nuclear material than to said cytoplasmic material and attains a selected infrared absorbance when so bound with said nuclear material, said stain including a thionin salt and a pH buffer solution,
    counterstaining the cellular material with a second stain having an infrared absorbance by cytoplasmic material which is distinguishably less than said infrared absorbance of nuclear material with said thionin stain,
    illuminating the stained cellular material with energy in the infrared spectrum, and
    imaging the stained cellular material in response to output infrared energy from the stained cellular material due to said infrared illumination.

2. The method of claim 1 wherein said imaging step includes detecting said output energy with an opto-electric transducer.

3. The method of claim 1 wherein said counterstaining step involves staining with a counterstain compound to produce stained cellular material wherein the cytoplasmic material is relatively transparent to said infrared illumination.

4. The method of claim 1 wherein the pH is acidic.

5. The method of claim 1 wherein said imaging step comprises digitizing said output energy.

6. The method of claim 5 further comprising the step of pathologically testing said digitized image information.

7. The method of claim 6 wherein said testing step comprises classifying said cellular material.

8. The method of claim 6 wherein said testing comprises a cytological analysis.

9. The method of claim 6 wherein said testing comprises a histological analysis.

10. The method of claim 1 wherein said staining step includes preparing a thionin stain consisting essentially of a thionin salt, an organic solvent, and a pH buffer.

11. The method of claim 10 wherein said organic solvent is selected from the group consisting of low molecular weight alcohols and DMSO.

12. The method of claim 11 wherein said organic solvent is selected from the group consisting of methanol, ethanol, isopropyl alcohol and DMSO.

13. A method of staining cellular material to contrast nuclear material from cytoplasmic material, thereby producing stained cellular material suitable for automated machine analysis and for imaging the stained cellular material, said method comprising the steps of
    preparing a thionin stain consisting essentially of a thionin salt, an organic solvent, and a pH buffer, said thionin stain having a predetermined pH in the range selected from about pH 4 to about pH 9 such that said thionin stain binds distinguishably more to said nuclear material than to said cytoplasmic material and attains a selected infrared absorbance when so bound with said nuclear material,
    staining the cellular material with said thionin stain for staining the nuclear material to have at least selected opacity to infrared energy and the cytoplasmic material to have a lesser opacity to infrared energy,
    preparing a Papanicolaou-type counterstain consisting essentially of a first staining solution, a second staining solution, and alcoholic rinses,
    wherein said first staining solution consists essentially of an orange dye, an alcoholic solvent, and pH buffer, and
    wherein said second staining solution consists essentially of a green dye, a red dye, a pH buffer, and an alcoholic solvent,
    counterstaining the cellular material, subsequent to said thionin-staining step, with said Papanicolaou-type counterstain,
    illuminating the stained cellular material, subsequent to said counterstaining step, with energy in the infrared spectrum, and imaging the output radiant infrared energy from said stained cellular material in response to said infrared illumination.

14. A method of staining cellular material to contrast the nuclear material from the cytoplasmic material, thereby producing stained cellular material suitable for automated machine analysis and for imaging the stained cellular material, said method comprising the steps of preparing a thionin stain consisting essentially of a thionin salt, an organic solvent, and a pH buffer, said thionin stain having a predetermined pH in the range selected from about pH 4 to about pH 9 such that said thionin stain binds distinguishably more to said nuclear material than to said cytoplasmic material and attains a selected infrared absorbance when so bound with said nuclear material, staining the cellular material with said thionin stain for staining the nuclear material to have at least selected opacity to infrared energy and the cytoplasmic material to have a lesser opacity to infrared energy, preparing an eosin-type counterstain consisting essentially of an Eosin Y dye, an organic solvent, and a pH buffer, counterstaining the cellular material, subsequent to said thionin-staining step, with said eosin-type counterstain, illuminating the stained cellular material, subsequent to said counterstaining step, with energy in the infrared spectrum, and imaging the output radiant infrared energy from said stained cellular material in response to said infrared illumination.

15. A method of staining cellular material for contrasting nuclear material from cytoplasmic material, for producing stained cellular material suitable for automated machine analysis and for imaging the stained cellular material, said method comprising the successive steps of staining the cellular material with an organic thionin stain, having a predetermined pH in the range selected from about pH 4 to about ph 9 such that said thionin stain binds distinguishably more to said nuclear material than to said cytoplasmic material and attains a selected infrared absorbance when so bound with said nuclear material, said stain including a thionin salt and a buffer solution, counterstaining the cellular material with a second stain having a near-infrared absorbance by cytoplasmic material which is distinguishably less than said near-infrared absorbance of nuclear material with said thionin stain, illuminating the stained cellular material with energy in the near-infrared spectrum, and imaging the stained cellular material in response to output energy from the stained cellular material due to said near-infrared illumination.

* * * * *